US011090100B2

(12) United States Patent
Sheth

(10) Patent No.: US 11,090,100 B2
(45) Date of Patent: Aug. 17, 2021

(54) CATHETER WITH MICRO-PELTIER COOLING COMPONENTS

(71) Applicant: Biosense Webster (Israel) LTD., Yokneam (IL)

(72) Inventor: Piyush Sheth, Porter Ranch, CA (US)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 485 days.

(21) Appl. No.: 15/202,562

(22) Filed: Jul. 5, 2016

(65) Prior Publication Data

US 2018/0008332 A1    Jan. 11, 2018

(51) Int. Cl.
*A61B 18/02* (2006.01)
*A61L 29/02* (2006.01)
(Continued)

(52) U.S. Cl.
CPC .............. *A61B 18/02* (2013.01); *A61L 29/02* (2013.01); *A61L 29/14* (2013.01);
(Continued)

(58) Field of Classification Search
CPC .......... A61B 18/02; A61B 2018/00047; A61B 2018/0237; A61B 2018/0243; A61B 2018/025; A61B 2018/00005; A61B 2018/0262; A61B 201/00023; A61B 201/00047; A61B 201/00083; A61B 201/00095; A61B 201/0022; A61B 201/00345; A61B 201/00351; A61B 201/00577; A61B 201/0212;
(Continued)

(56) References Cited

U.S. PATENT DOCUMENTS 4,860,744 A * 8/1989 Johnson ............... A61B 18/082
606/31
5,207,674 A * 5/1993 Hamilton ............... A61B 18/02
606/20

(Continued)

OTHER PUBLICATIONS

European Patent Office Search Report for EP App. No. 17179571.9, dated Nov. 7, 2017, 13 pgs.

*Primary Examiner* — Eun Hwa Kim
*Assistant Examiner* — Catherine Premraj
(74) *Attorney, Agent, or Firm* — Lewis Roca Rothgerber Christie LLP

(57) ABSTRACT

A catheter has a cooling distal section for freezing tissue to sub-zero temperatures with one or more miniature reverse thermoelectric or Peltier elements, also referred to herein as micro-Peltier cooling (MPC) units or electrodes. The MPC units may be on outer surface of an inflatable or balloon member or a tip electrode shell wall that has a fluid-containing interior cavity acting as a heat sink. Each MPC unit has a hot junction and a cold junction whose temperatures are regulated by the heat sink, and a voltage/current applied to the MPC units. A temperature differential of about 70 degrees Celsius may be achieved between the hot and cold junctions for extreme cooling, especially where the MPC units include semiconductor materials with high Peltier co-efficients. An outer coating of thermally-conductive but electrically-insulative material seals the MPC units to prevent unintended current paths through the MPC units.

20 Claims, 13 Drawing Sheets

(51) Int. Cl.
*A61L 29/14* (2006.01)
*A61M 25/01* (2006.01)
*H01L 35/16* (2006.01)
*H01L 35/18* (2006.01)
*H01L 35/22* (2006.01)
*H01L 35/30* (2006.01)
*H01L 35/32* (2006.01)
*A61B 18/00* (2006.01)
*A61B 18/14* (2006.01)

(52) U.S. Cl.
CPC ......... *A61M 25/0136* (2013.01); *H01L 35/16* (2013.01); *H01L 35/18* (2013.01); *H01L 35/22* (2013.01); *H01L 35/30* (2013.01); *H01L 35/32* (2013.01); *A61B 2018/0016* (2013.01); *A61B 2018/0022* (2013.01); *A61B 2018/00023* (2013.01); *A61B 2018/00047* (2013.01); *A61B 2018/00083* (2013.01); *A61B 2018/00095* (2013.01); *A61B 2018/00345* (2013.01); *A61B 2018/00351* (2013.01); *A61B 2018/00577* (2013.01); *A61B 2018/025* (2013.01); *A61B 2018/0212* (2013.01); *A61B 2018/0293* (2013.01); *A61B 2018/1435* (2013.01)

(58) Field of Classification Search
CPC .......... A61B 201/025; A61B 201/0293; A61B 201/1435; A61L 29/02; A61L 29/14; A61M 25/0136; H01L 35/16; H01L 35/18; H01L 35/22; H01L 35/30; H01L 35/32
See application file for complete search history.

(56) References Cited

U.S. PATENT DOCUMENTS

| | | | |
|---|---|---|---|
| 5,281,213 A | | 1/1994 | Milder et al. |
| 5,281,215 A | | 1/1994 | Milder |
| 5,423,807 A | | 6/1995 | Milder |
| 5,967,967 A | * | 10/1999 | Guo ........................ A61N 1/26 600/13 |
| 5,967,976 A | * | 10/1999 | Larsen ................. A61B 5/0422 600/374 |
| 6,176,857 B1 | * | 1/2001 | Ashley ................... A61B 18/08 606/32 |
| 8,287,532 B2 | | 10/2012 | Carroll et al. |
| 9,101,733 B2 | | 8/2015 | McDaniel |
| 2001/0014802 A1 | * | 8/2001 | Tu ......................... A61B 18/02 606/21 |
| 2003/0014098 A1 | * | 1/2003 | Quijano ................ A61B 5/053 607/122 |
| 2005/0203505 A1 | * | 9/2005 | Megerman ............ A61B 18/02 606/41 |
| 2011/0307034 A1 | * | 12/2011 | Hastings ........... A61B 18/1206 607/61 |
| 2012/0029512 A1 | | 2/2012 | Willard et al. |
| 2012/0265188 A1 | * | 10/2012 | Buchbinder ............ A61F 7/123 606/21 |
| 2013/0197499 A1 | * | 8/2013 | Lalonde ................ A61B 18/02 606/21 |
| 2013/0204241 A1 | * | 8/2013 | Baust .................... A61B 18/02 606/24 |

* cited by examiner

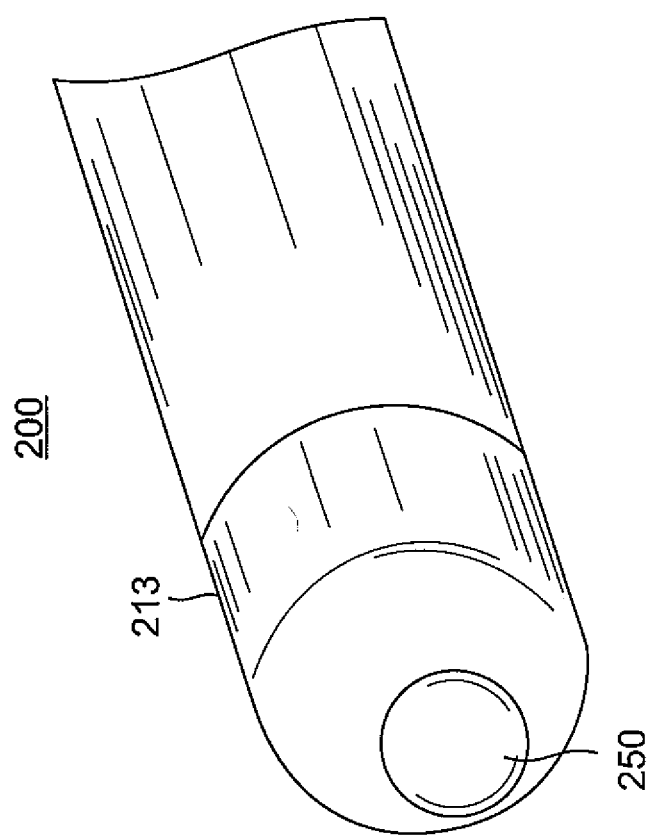

CATHETER WITH MICRO-PELTIER COOLING COMPONENTS

FIELD OF INVENTION

This invention relates to electrophysiologic (EP) catheters, in particular, EP catheters for mapping and/or ablation in the heart.

BACKGROUND

Many medical procedures are performed using minimally invasive surgical techniques wherein one or more slender implements are inserted through one or more small incisions into a patient's body. With respect to ablation, the surgical implement may include a rigid or flexible structure having an ablation device at or near its distal end that is placed adjacent to the tissue to be ablated. Radio frequency energy, microwave energy, laser energy, extreme heat, and extreme cold may be provided by the ablation device to destroy the tissue.

With respect to cardiac procedures, cardiac arrhythmia may be treated through selective ablation of cardiac tissue to eliminate the source of the arrhythmia. A popular minimally invasive procedure, radio frequency (RF) catheter ablation, includes a preliminary step of conventional mapping followed by the creation of one or more ablated regions (lesions) in the cardiac tissue using RF energy. Multiple lesions are frequently required. Often, five lesions, and sometimes as many as twenty lesions may be required before a successful result is attained. Sometimes only one of the lesions is actually effective.

Deficiencies of radio frequency ablation devices and techniques have been to some extent overcome by cryogenic mapping and ablation. Such cryogenic mapping techniques are in U.S. Pat. Nos. 5,423,807; 5,281,213 and 5,281,215. However, even though combined cryogenic mapping and ablation devices often times permit greater certainty and less tissue damage than RF devices and techniques, both cryogenic and RF ablation devices are usually configured for spot or circular tissue ablation.

Spot tissue ablation is acceptable for certain procedures. However, other procedures may be more therapeutically effective if multiple spot lesions are made simultaneously, such as in a circumferential pattern in a tubular region and/or the ostium thereof. In that regard, catheters with inflatable assemblies or balloons are known. Such balloons may include electrodes positioned on the outer surface of the balloons for ablating tissue and are typically inflated with a pressurized fluid source. With cryoablation, reversible freezing of tissue occurs at a temperature of about −10 C (about +14 F), and permanent tissue ablation occurs at a temperature of about −73 C (about −99.4 F). However, where cooling fluids are passed through the cryogenic catheter while inside a patient's body, the use of sub-freezing coolants may not be ideal.

Accordingly, a need exists for a cryoablation catheter having an inflatable member or balloon, with significantly improved cooling efficiency yet reduced risks of health hazards to the patient and attending physicians and assistants from exposure to or contact with sub-freezing coolants.

SUMMARY OF THE INVENTION

Features of the present invention include a catheter having a cooling distal section for freezing heart tissue to sub-zero temperatures with one or more miniature reverse thermoelectric or Peltier elements, also referred to herein as micro-Peltier cooling (MPC) units or electrodes. The MPC units may be provided on an outer surface of a distal section member of the catheter, such as an inflatable or balloon member or a shell wall that can advantageously provide an interior cavity which can contain fluid so as to function as a heat sink for the MPC units. Each MPC unit has a hot side/junction and a cold side/junction whose temperatures are regulated by the heat sink, and a voltage/current applied to the one or more MPC units. A temperature differential of about 70 degrees Celsius may be achieved between the hot and cold sides/junctions for extreme cooling of tissue via contact with or exposure to the cold sides of the one or more MPC units, especially where the MPC units include semiconductor materials with high Peltier co-efficients. The MPC units may be arranged in a variety of patterns on the contact surface. An outer coating of thermally-conductive but electrically-insulative material seals the one or more MPC units against exposure to blood and other conductive tissue or fluids which may cause unintended current paths through the MPC units.

Embodiments of the present invention include an electrophysiology catheter for use in a patient's vasculature, comprising an elongated catheter body and a distal section having a micro-Peltier cooling (MPC) unit. The MPC unit has a hot junction and a cold junction, a thermally-conductive and electrically-nonconductive layer on the cold junction sealing the cold junction from exposure to blood in the vasculature, and a thermally-conductive and electrically-nonconductive substrate supporting the MPC unit, wherein the hot junction is in closer proximity to the substrate and the cold junction is in closer proximity to the layer. The distal section also has an interior cavity configured to receive a fluid having a predetermined temperature, wherein the cavity is configured to position the fluid for thermal conduction between the fluid and the hot junction across the substrate. The catheter is configured for current flow through the cold and hot junctions of the MPC unit.

In some detailed embodiments, the current flows from a first N-type semiconductor to a last P-type semiconductor.

In some detailed embodiments, the distal section includes an inflatable balloon member having a membrane defining the interior cavity, wherein at least a portion of the membrane forms the substrate.

In some detailed embodiments, the distal section includes a distal tip shell having a shell wall defining the interior cavity, wherein at least a portion of the shell wall forms the substrate.

In some detailed embodiments, the cold junction includes an electrically-conductive material, preceded by an N-type semiconductor material, and followed by a P-type semiconductor material, connected in series.

In some embodiments, the hot junction includes an electrically-conductive material, preceded by P-type semiconductor material, and followed by an N-type semiconductor material, connected in series.

In some embodiments, the P-type semiconductor material comprises bismuth telluride, silicon-germanium and/or bismuth-antimony.

In some embodiments, the N-type semiconductor material comprises bismuth telluride, silicon-germanium and/or bismuth-antimony.

In some embodiments, the temperature of the fluid ranges between about 10 C degrees Celsius and −10 degrees Celsius.

In some embodiments, the catheter further comprises a control handle and a voltage/current source providing the current flow is housed in the control handle.

Other embodiments of the present invention include an electrophysiology catheter for insertion into a patient's vasculature, comprising an elongated catheter body, a distal section distal of the catheter body, the distal section having an outer surface layer configured for contact with tissue, the contact surface layer being thermally conductive and electrically nonconductive, a control handle proximal of the catheter body, and a micro-Peltier cooling (MPC) unit. The MPC units has a first wire of a first material having a distal end in the distal section, and a proximal end proximal of the distal section, and a second wire of a second material having a distal end in the distal section, and a proximal end proximal of the distal section. The MPC unit also has a cold junction comprising an electrically conductive connection of the distal ends of the first and second wires, wherein the cold junction is positioned in the distal section and thermally coupled to the outer surface layer, and a hot junction comprising an electrically conductive connection of the proximal ends of the first and second wires, wherein the hot junction is positioned proximally of the cold junction. The MPC unit further has a heat sink thermally coupled to the hot junction, wherein the heat sink having a predetermined temperature, wherein the catheter is configured for current flow through the MPC unit.

In some detailed embodiments, the distal section includes a distal needle thermally coupled to the cold junction, and an outer surface layer of the distal needle provides the outer surface layer.

In some detailed embodiment, the hot junction is proximal of the control handle.

In some detailed embodiments, the heat sink includes a fluid reservoir.

In some detailed embodiments, the predetermined temperature of the heat sink ranges between about 10 degrees Celsius and −10 degrees Celsius.

In some detailed embodiments, the first material includes an N-type semiconductor material comprising bismuth telluride, silicon-germanium and/or bismuth-antimony.

In some detailed embodiments, the first material includes a P-type semiconductor material comprising bismuth telluride, silicon-germanium and/or bismuth-antimony.

Further embodiments of the present invention include an electrophysiology catheter for insertion into a patient's vasculature, comprising an elongated catheter body, and a distal section distal of the catheter body, wherein the distal section has a distal probe portion with an outer surface layer configured for tissue contact and the outer surface layer is thermally-conductive and electrically-nonconductive. The catheter also includes a control handle proximal of the catheter body, and a micro-Peltier cooling (MPC) unit. The MPC unit has a first wire of a first material having a distal end in the distal section, and a proximal end proximal of the distal section, and a second wire of a second material having a distal end in the distal section, and a proximal end proximal of the distal section. The MPC unit further has a cold junction and a hot junction. The cold junction comprises an electrically-conductive material in a tubular configuration forming the distal probe portion, the electrically-conductive material couples the distal ends of the first and second wires, and the cold junction is thermally coupled to the outer surface layer. The hot junction comprises an electrically conductive connection of the proximal ends of the first and second wires, wherein the hot junction is positioned proximally of the cold junction. The MPC unit also includes a heat sink thermally coupled to the hot junction, wherein the heat sink has a predetermined temperature.

In some detailed embodiments, the first material includes an N-type semiconductor material comprising bismuth telluride, silicon-germanium and/or bismuth-antimony.

In some detailed embodiments, the first material includes a P-type semiconductor material comprising bismuth telluride, silicon-germanium and/or bismuth-antimony.

BRIEF DESCRIPTION OF THE DRAWINGS

These and other features and advantages of the present invention will be better understood by reference to the following detailed description when considered in conjunction with the accompanying drawings wherein:

FIG. 13 is a perspective view of a distal end of a focal cryoablation catheter, having one MPC unit, according to an embodiment of the present invention.

DETAILED DESCRIPTION OF THE INVENTION

Figure 1:
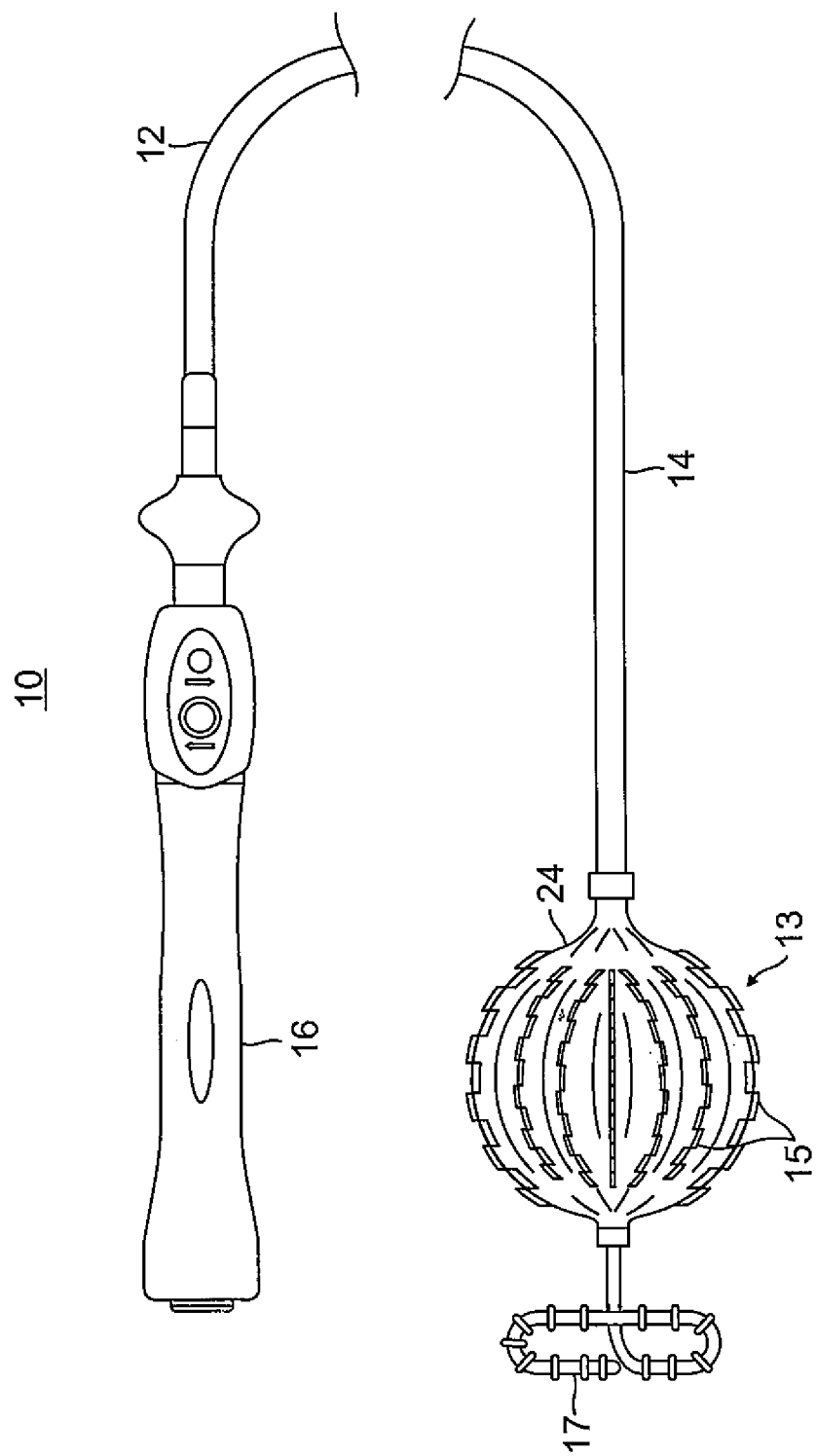
FIG. 1 is a top plan view of a catheter of the present invention, having an inflatable cryoablation assembly, according to an embodiment.
Figure 2:
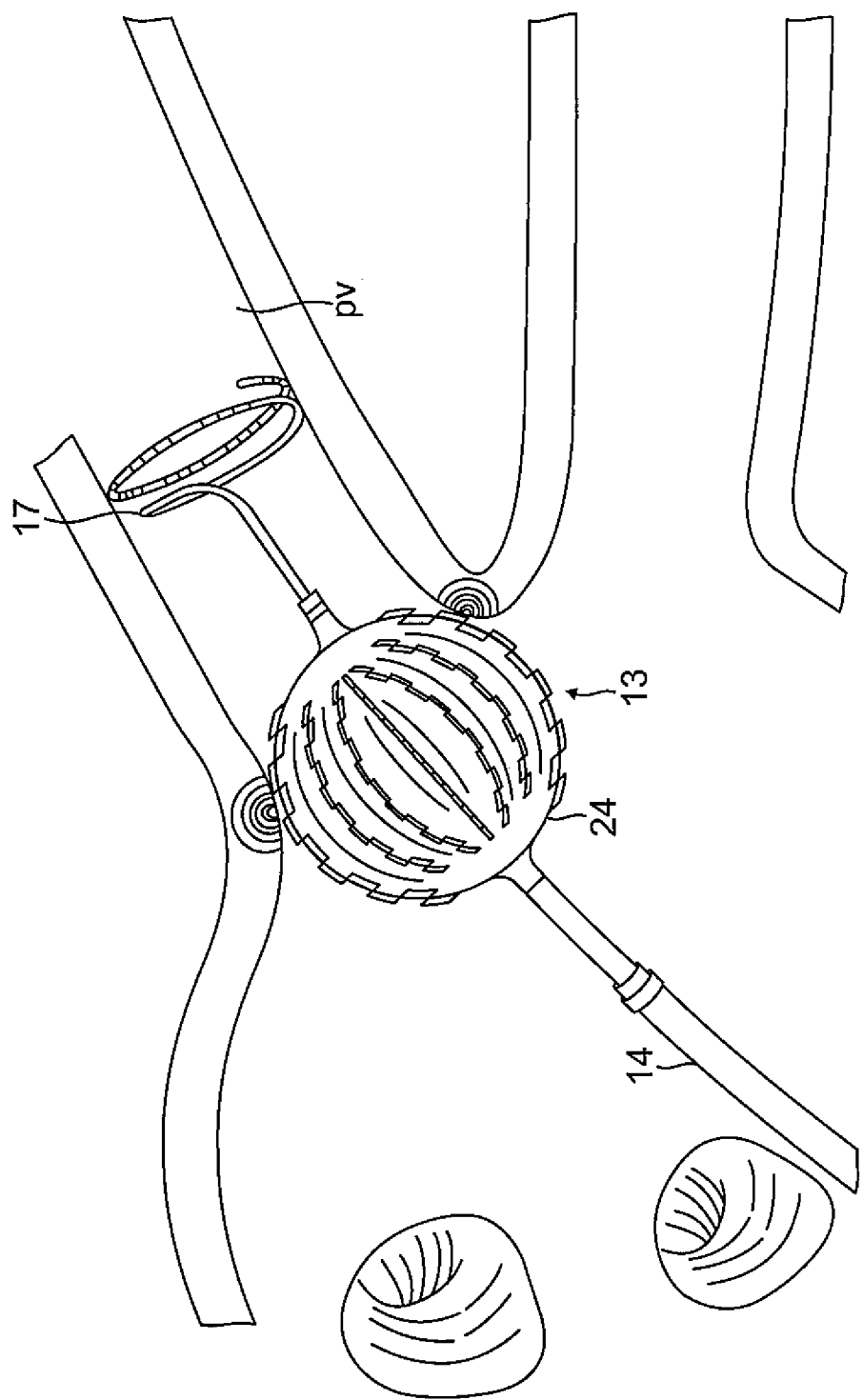
FIG. 2 is a schematic representation of the electrode assembly of FIG. 1, inflated and positioned in or near an ostium of a pulmonary vein.

As shown in FIG. 1, a catheter 10 comprises an elongated catheter body 12, a distal section having an inflatable cryoablation assembly 13 with a balloon member 24 and one or more micro-Peltier cooling modules 15 in and/or on its outer surface, and a deflection control handle 16 attached to the proximal end of the catheter body 12. The catheter 10 may function in combination with a further distal electrode assembly, for example, a lasso electrode assembly 17, for which the inflatable assembly 13 can function as an anchor and/or stabilizer when the lasso electrode assembly 17 is in use, such as when inserted in a pulmonary vein PV of the left atrium, as shown in FIG. 2.

Figure 3:
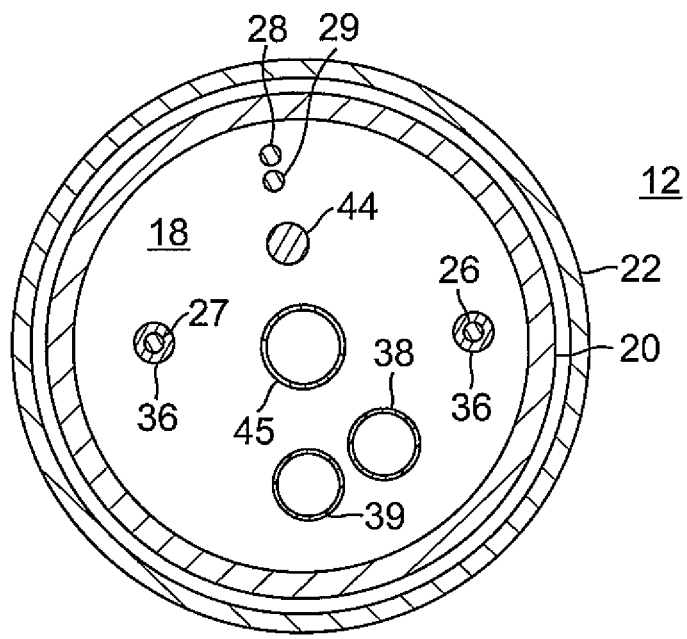
FIG. 3 is an end cross-sectional view of a catheter body 12, according to an embodiment of the present invention.

The catheter body 12 comprises an elongated tubular construction, having a single, axial or central lumen 18, as shown in FIG. 3. The catheter body 12 is flexible, i.e., bendable, but substantially non-compressible along its length. The catheter body 12 can be of any suitable construction and made of any suitable material. A presently preferred construction comprises an outer wall 22 made of a polyurethane, or PEBAX. The outer wall 22 comprises an imbedded braided mesh of high-strength steel, stainless steel or the like to increase torsional stiffness of the catheter body 12 so that, when the control handle 16 is rotated, the tip section 14 of the catheter 10 will rotate in a corresponding manner.

The outer diameter of the catheter body 12 is not critical, but is preferably no more than about 8 french, more preferably about 7 french. Likewise the thickness of the outer wall 22 is not critical, but is thin enough so that the central lumen 18 can accommodate components, including, for example, one or more puller wires, electrode lead wires, irrigation tubing, and any other wires and/or cables. The inner surface of the outer wall 22 is lined with a stiffening tube 20, which can be made of any suitable material, such as polyimide or nylon. The stiffening tube 20, along with the braided outer wall 22, provides improved torsional stability while at the same time minimizing the wall thickness of the catheter, thus maximizing the diameter of the central lumen 18. The outer diameter of the stiffening tube 20 is about the same as or slightly smaller than the inner diameter of the outer wall 22. Polyimide tubing is presently preferred for the stiffening tube 20 because it may be very thin walled while still providing very good stiffness. This maximizes the diameter of the central lumen 18 without sacrificing strength and stiffness. As would be recognized by one skilled in the art, the catheter body construction can be modified as desired. For example, the stiffening tube can be eliminated.

Figure 4:
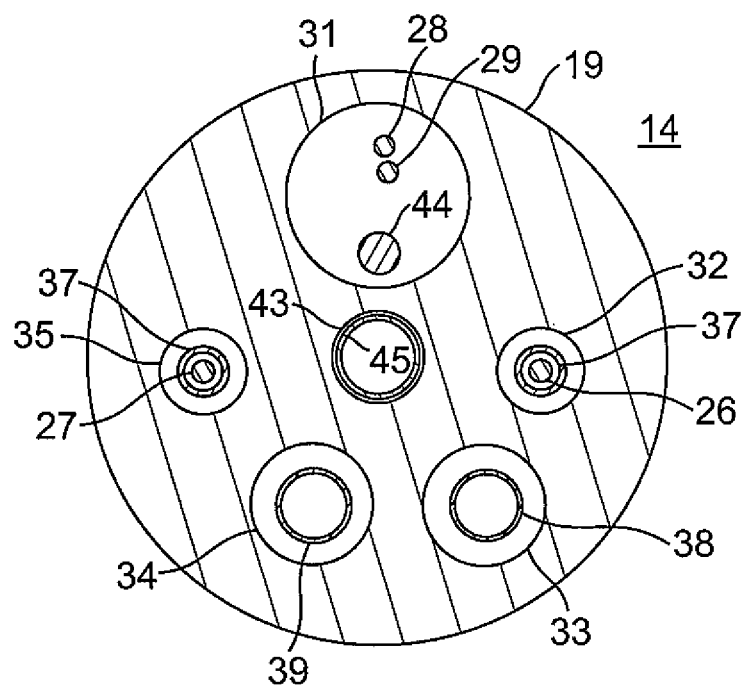
FIG. 4 is an end cross-sectional view of an intermediate deflection section, according to an embodiment of the present invention.

The intermediate deflection section comprises a shorter section of tubing 19, which as shown in FIG. 4, has multiple lumens, for example, off-axis lumens 31, 32, 33 and 34. In some embodiments, the tubing 19 is made of a suitable non-toxic material more flexible than the catheter body 12. A suitable material for the tubing 19 is braided polyurethane, i.e., polyurethane with an embedded mesh of braided high-strength steel, stainless steel or the like. The outer diameter of the deflection section 14 is similar to that of the catheter body 12. The size of the lumens is not critical and can vary depending on the specific application.

Various components extend through the catheter 10. In some embodiments, as shown in FIG. 3 and FIG. 4, the components include one pair of lead wires 28 and 29 for each micro-Peltier cooling module 15. The components also include one or more puller wires 26 and 27 for deflecting the deflection section 14, a cable 44 for an electromagnetic position sensor 46 (not shown) housed in suitable location in a distal portion of the catheter. The components further include a feeder fluid tubing 38 for passing fluid distally along the catheter and into the balloon member 24 for inflation and cooling, a return fluid tubing 39 for passing fluid from the balloon member proximally along the catheter, and a guidewire tubing 45. These components pass through the central lumen 18 of the catheter body 12, as shown in FIG. 3.

It is understood that a return fluid tubing is optional where fluid is used for balloon member inflation purposes during procedures of shorter duration, for example, about 10 mins or less. For procedures of longer duration, the feeder fluid tubing 38 and the return fluid tubing 39 enable circulation of the fluid within the balloon member to maintain efficacy of cryogenic cooling of the micro-Peltier modules.

In the deflection section 14, different components pass through different lumens of the tubing 19 as shown in FIG. 4. In some embodiments, the lead wires 28 and 29 and cable 44 for electromagnetic position sensor 46 pass through first lumen 31. The first puller wire 26 passes through second lumen 32. The feeder fluid tubing 38 passes through third lumen 33. The return fluid tubing 39 passes through a fourth lumen 34. A second puller wire 27 passes through fifth lumen 35. The guidewire tubing 45 passes through a sixth lumen 43. The second and fifth lumens 32 and 35 are diametrically opposite of each other to provide bi-directional deflection of the intermediate deflection 14.

The distal ends of the puller wires 26 and 27 can be attached to sidewall of the tubing 19 at or near its distal end, for example, with the use of T-bars, as known in the art. Such a design is described in U.S. Pat. No. 9,101,733, the entire disclosure of which is incorporated herein by reference. Each puller wire 26 and 27 is anchored at its proximal end in the control handle 16. In some embodiments, the puller wires are made of any suitable metal, such as stainless steel or Nitinol, and are preferably coated with Teflon® or the like. The coating imparts lubricity to the puller wires.

A compression coil 36 is situated within the catheter body 12 in surrounding relation to each puller wire 26 and 27, as shown in FIG. 3. The compression coils 36 extend from the proximal end of the catheter body 12 to at or near the proximal end of the deflection section 14. The compression coils 36 are made of any suitable metal, preferably stainless steel. Each compression coil is tightly wound on itself to provide flexibility, i.e., bending, but to resist compression. The inner diameter of the compression coil is preferably slightly larger than the diameter of the puller wire. A Teflon® coating on each puller wire allows it to slide freely within the compression coil. If desired, particularly if the lead wires 28 and 29 are not enclosed by a protective sheath, the outer surface of the compression coils 36 can be covered by a flexible, non-conductive sheath (not shown), e.g., made of polyimide tubing, to prevent contact between the compression coils 36 and any other wires within the catheter body 12.

The puller wire 26 extends through the second lumen 32 of the tubing 19 and the puller wire 27 extends through the fifth lumen 35 of the tubing 19. Within these lumens, each puller wire extends through a respective plastic, preferably Teflon®, sheath 37 (see FIG. 4), which prevents the puller wires from cutting into the wall of the tubing 19 when the deflection section 14 is deflected.

Longitudinal movement of the puller wires 26 and 27 relative to the catheter body 12, which results in deflection of the tip section 14, is accomplished by suitable manipulation of the control handle 16. A suitable control handle design for use with the present invention is described in U.S. Pat. No. 8,287,532, the entire disclosure of which is incorporated herein by reference. If desired, the catheter can be uni-deflectional, i.e., having only one puller wire.

Figure 5:
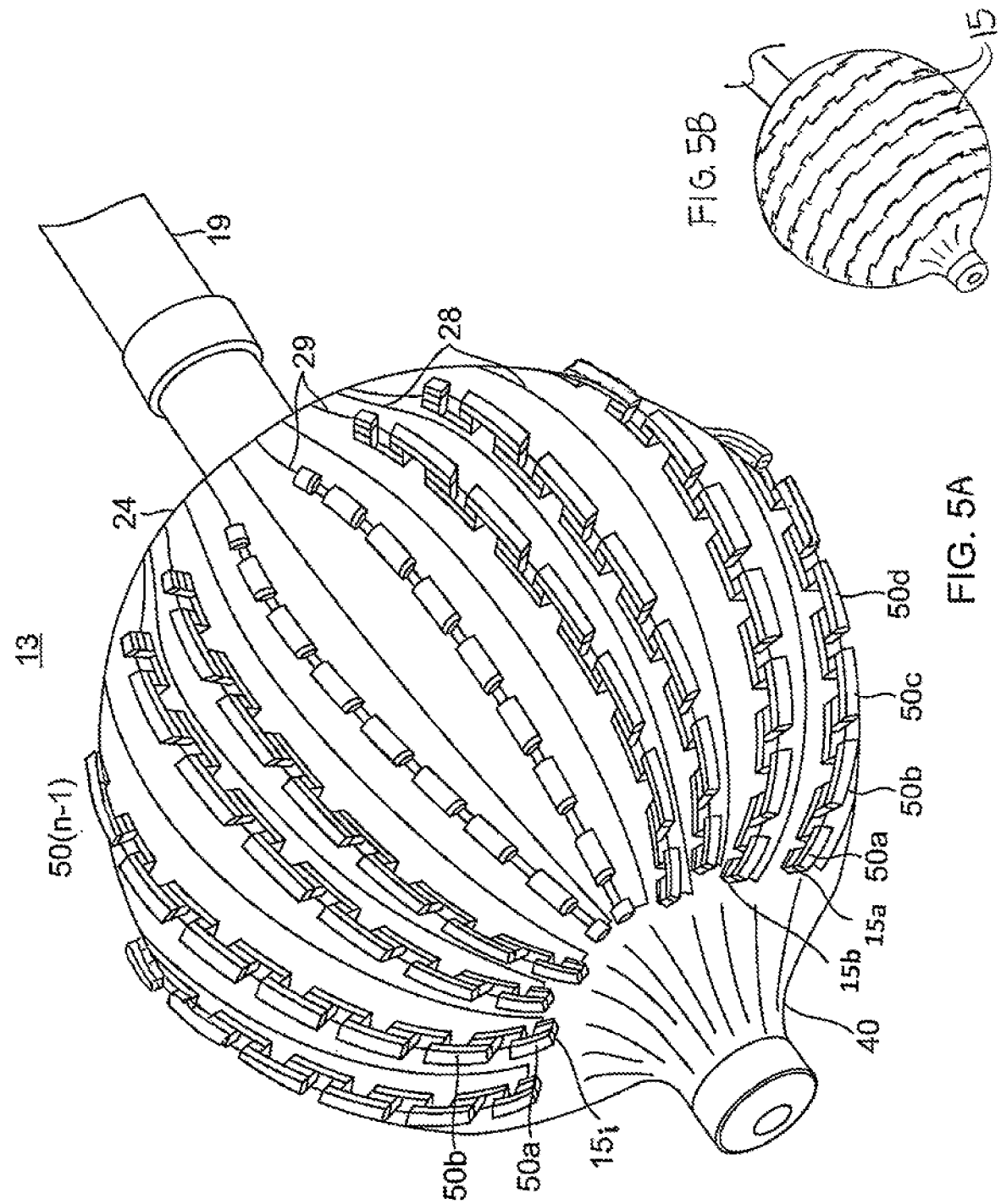
FIG. 5A is a detailed perspective view of the inflatable cryoablation assembly of FIG. 1, with one or more Micro-Peltier Cooling ("MPC") modules.
FIG. 5B is a perspective view of an inflatable cryoablation assembly, according to another embodiment of the present invention.

As shown in detail in FIG. 5A, distal of the deflection section 14 is the inflatable cryoablation assembly 13 including the balloon member 24 which can serve as a substrate on which one or more micro-Peltier modules 15 are provided. The balloon member 24 has a membrane 40 which is flexible and if appropriate or desired, also elastic.

Figure 6:
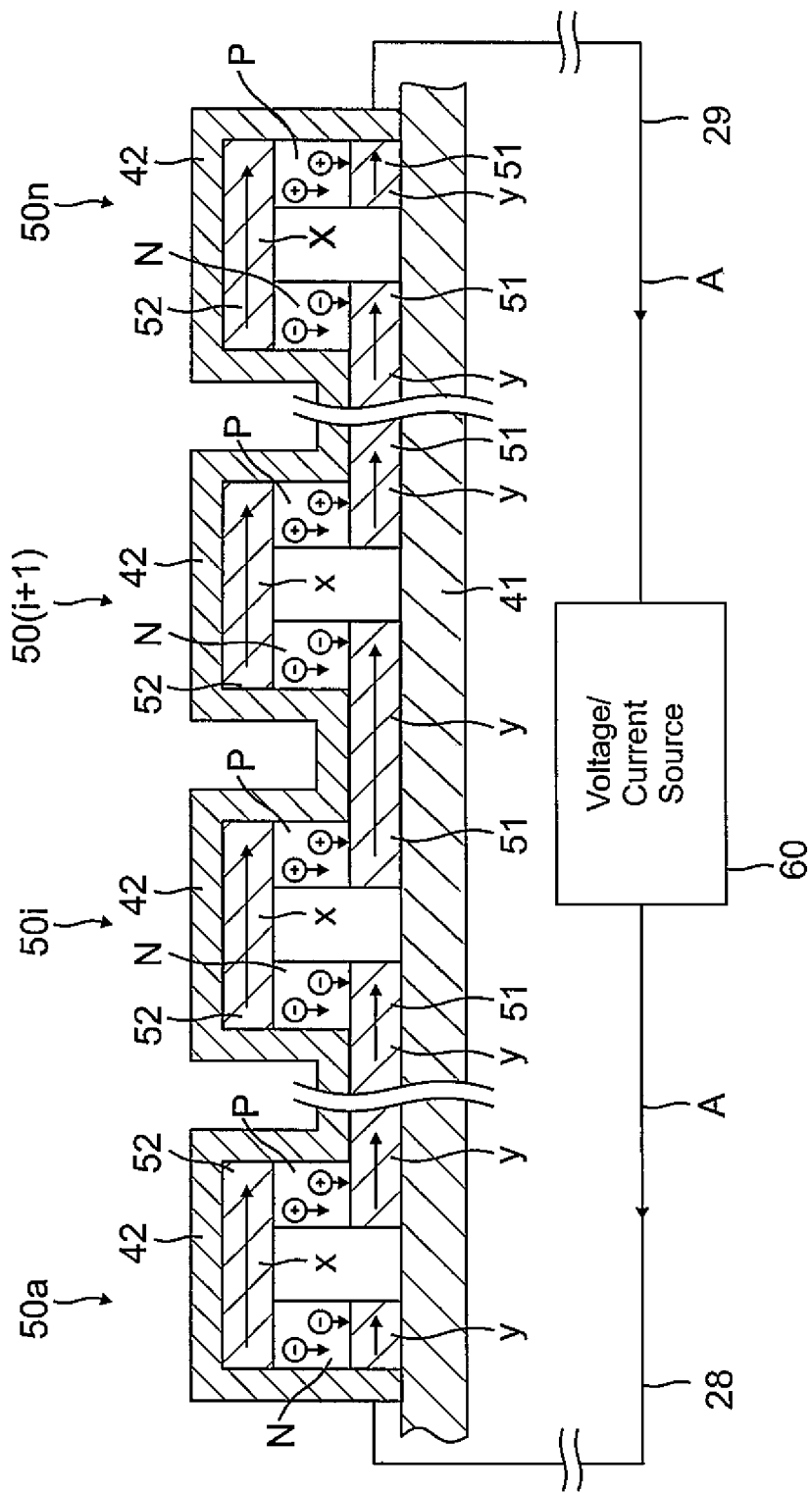
FIG. 6 is a side cross-sectional view of an MPC module, according to an embodiment of the present invention.

Fixedly attached to an outer surface of the balloon membrane 40 are one or more micro-Peltier cooling ("MPC") modules 15. As shown in FIG. 5A, each of MPC modules 15a-15i includes one or more MPC units 50a-50n (including the penultimate MPC unit 50(n−1) depicted in the figure). As shown in FIG. 6, each unit 50i has an N-type semiconductor N and a P-type semiconductor P that are configured thermally in parallel to each other by thermally-conducting layers or surfaces 41 and 42, and electrically in series at junctions X and Y defined by, respectively, first and second electrically-conducting members 51 and 52 at their opposing ends.

When a voltage is applied to the N-type and the P-type semiconductors of any unit 50i via the first and second electrically-conducting members 51 and 52 forming a circuit with a current/voltage source 60, a DC current flows across junctions X and Y of the N-type and P-type semiconductors (as shown by arrows A) causing a temperature difference between the junctions X and Y of the unit 50i. With the current/voltage source 60 and the circuit configured such that the current flows first into the N-type semiconductor and then out of the P-type semiconductor, the junction Y is the "hot" junction with the first surface 41 being the "hot" (or relatively hotter) side, and the junction X with the second surface 42 being the "cold" (or relatively colder) side, wherein the "cold/colder" side absorbs heat which is then moved to the other side of the unit 50i where the "hot/hotter" side is. Where the MPC unit 50 is configured such that the cold side 42 faces outwardly on the balloon membrane 40 of the balloon member 24, the cold side functions as cryoablation surface of the inflatable assembly 13 adapted for tissue contact. With the hot side 41 facing inwardly, it is in closer proximity to the balloon membrane 40 and hence adapted for thermal conduction (directly or indirectly) with a heat sink that includes heat-absorbing fluid entering and exiting the interior cavity 25 of the balloon member 24 via feeder fluid tubing 38 and return fluid tubing 39. Voltage/current source 60 of the Peltier circuit can be adjusted to create a temperature difference between the junctions X and Y ranging between about 50 degrees Celsius, preferably about 60 degrees Celsius, and, more preferably about 70 degrees Celsius. The fluid can be any suitable fluid, including, for example, water or saline. In some embodiments, the MPC circuit can be adjusted such that the hot side 41 is at body temperature, namely, about 37 Celsius, therefore achieving about −33 Celsius on the cold side 42. With chilled water or saline at about 0 C being the temperature of the hot side 41, the cold side 42 can be about −70 C which is a temperature well suited for cryoablation.

As shown in FIG. 5A and FIG. 6, one or more MPC units 50a-50n are cascaded together for form an MPC module 15 for lower temperature, with the N-type semiconductor of a first MPC unit 50a being connected to one hot wire 28 and the P-type semiconductor of a last MPC unit 50n being connected to a neutral wire 29 for forming one Peltier cooling circuit driven by the voltage/current source 60 with a current direction as shown by arrow A. As shown in FIG. 6, adjacent MPC units 50i and 50(i+1) of a MPC module 15 share a common "hot" junction Y such that the units 50a-50n are joined with current flowing from the P-type semiconductor of a downstream MPC unit 50i to the N-type semiconductor of an upstream MPC unit 50(i+1).

Figure 7:
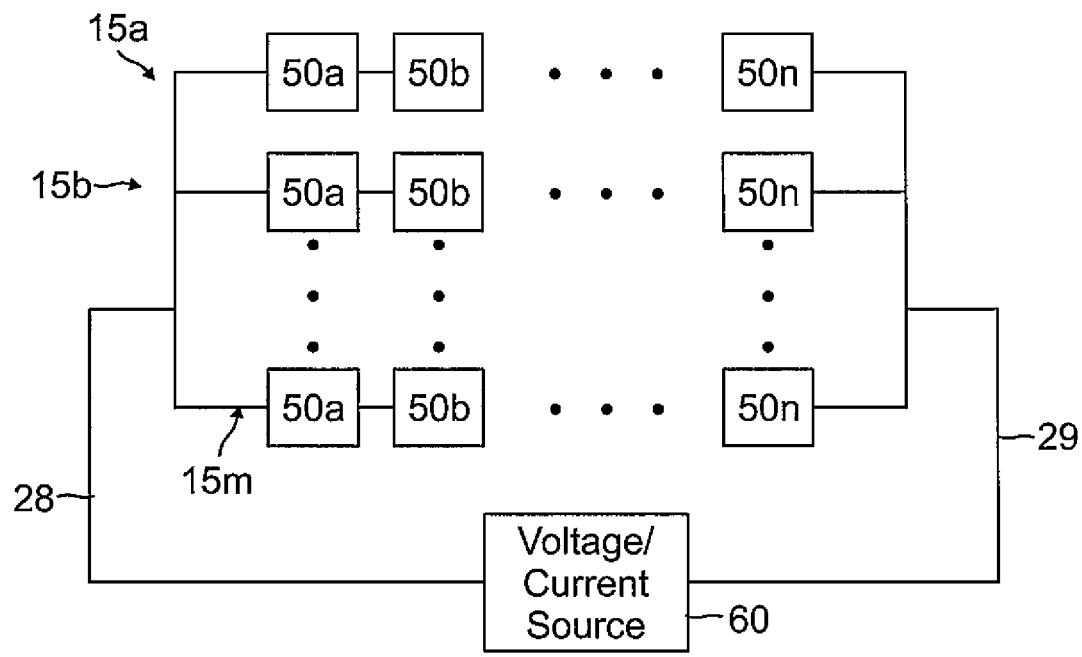
FIG. 7 is a block diagram of a circuit for the inflatable cryoablation assembly, according according to an embodiment of the present invention.
Figure 8:
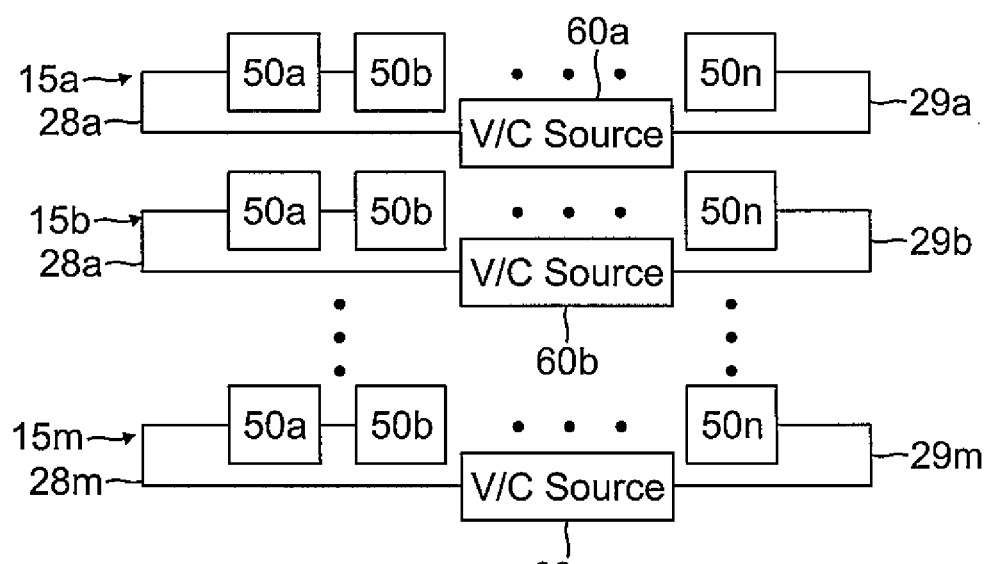
FIG. 8 is a block diagram of a circuit for the inflatable cryoablation assembly, according to another embodiment of the present invention.

With a plurality of n MPC units 50 and a plurality of m MPC modules 15, a matrix of "n×m" MPC units 50 may be provided on any tissue contacting surface of a catheter, as shown in FIG. 7. The MPC modules 15a-15m can be connected in parallel, all driven by a single voltage/current source 60 via a pair of lead wires 28 and 29. In other embodiments, each MPC module 15i of MPC modules 15a-15m may have its respective voltage/current source 60i (of voltage/current sources 60a-60m), and lead wires 28i (of lead wires 28a-28m) and 29i (of lead wires 29a-29m), as shown in FIG. 8. It is understood that a catheter may have any one or more combinations of MPC modules sharing a voltage/current source, as desired or appropriate.

The assembly 13 includes one or more feeder and return lead wires 28 and 29. They may extend along the outer surface of the balloon membrane 40, affixed thereto, to reach the first and last MPC units 50a and 50n of each MPC module 15i, as shown in FIG. 5A. As described hereinabove, the lead wires 28 and 29 extend through the central lumen 18 of the catheter shaft 12 and the first lumen 31 of the tubing 19 of the deflection 14 before emerging through apertures (not shown) formed in, for example, the wall of a distal section of the tubing 19. In an alternate embodiment, the lead wires 28 and 29 may extend into the interior cavity 25 of the balloon member 13 and emerge through fluid-tight apertures (not shown) formed in the balloon membrane 40.

Figure 9:
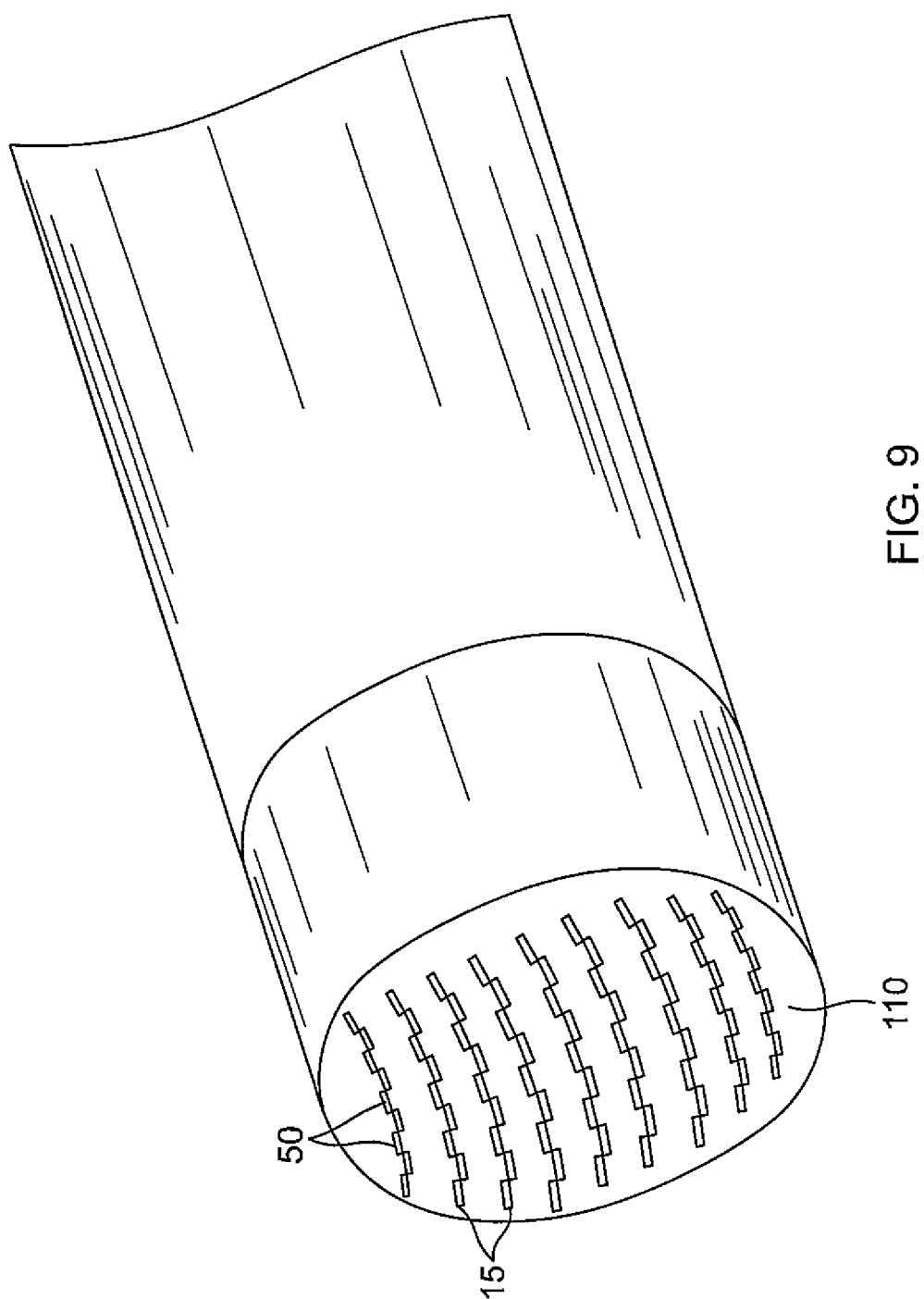
FIG. 9 is a perspective view of a distal end of a focal cryoablation catheter, according to according to an embodiment of the present invention.
Figure 10:
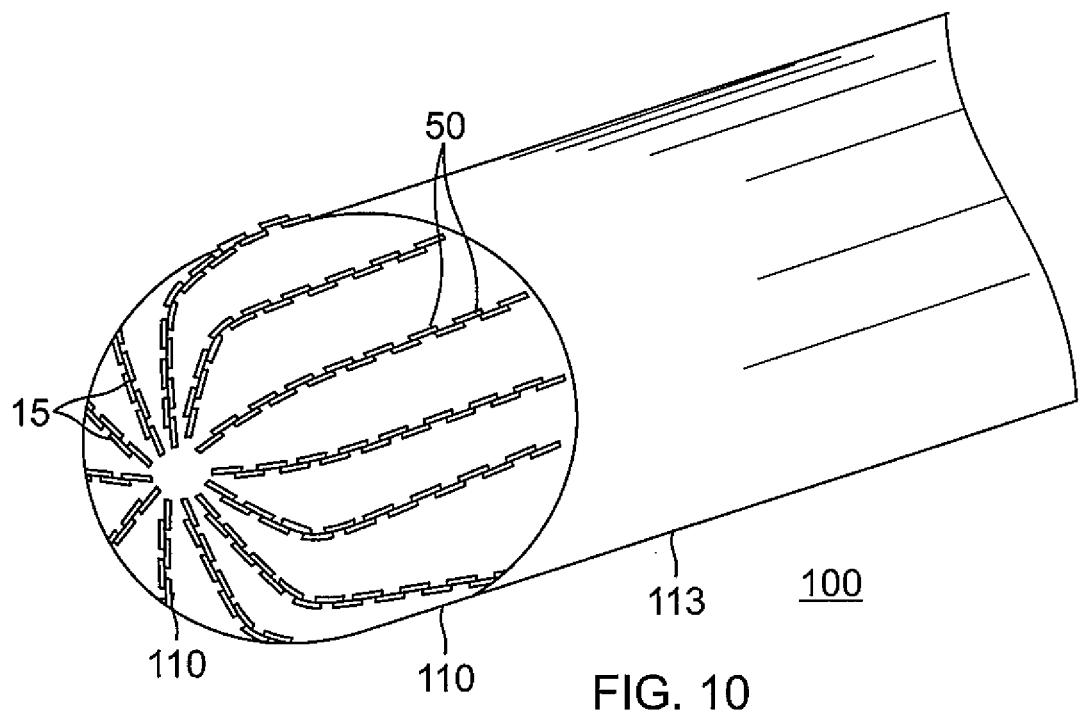
FIG. 10 is a perspective view of a distal end of a focal cryoablation catheter, according to another embodiment of the present invention.
Figure 11:
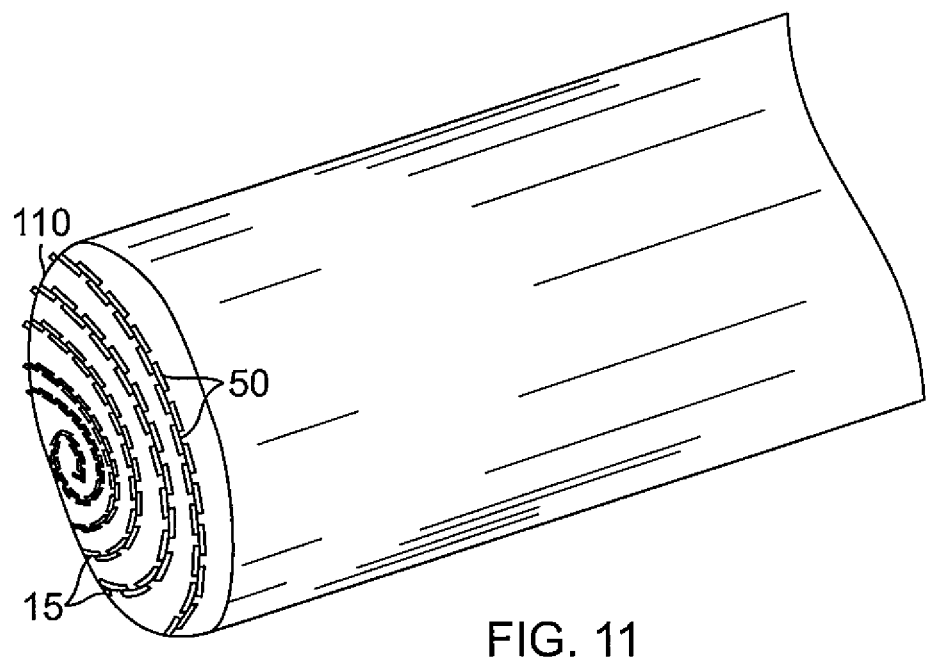
FIG. 11 is a perspective view of a distal end of a focal cryoablation catheter, according to another embodiment of the present invention

In other embodiments as shown in FIG. 9, FIG. 10 and FIG. 11, a focal catheter 100 has a distal tip section 113 having one or more end and/or side surfaces 110 adapted for tissue contact. Provided on the surfaces 110 are one or more MPC units 50 forming one or more one or more MPC modules 15. The one or more units 50 and modules 15 may be arranged in any suitable pattern, including, for example, linear, nonlinear, circular, concentric, nonconcentric patterns and combinations thereof. FIG. 9 illustrates an embodiment of a parallel linear pattern on a distal end surface of the catheter. FIG. 10 illustrates an embodiment of longitudinal radial patterns on distal end and circumferential surfaces of the catheter. FIG. 11 illustrates an embodiment of a circular spiral pattern on a distal dome surface. While the MPC modules 15 of FIG. 5A are arranged in a longitudinal pattern in FIG. 5A, the MPC modules 15 of FIG. 5B are arranged in a latitudinal pattern which is suited for ablating ring lesions in an ostium of a pulmonary vein.

Figure 12:
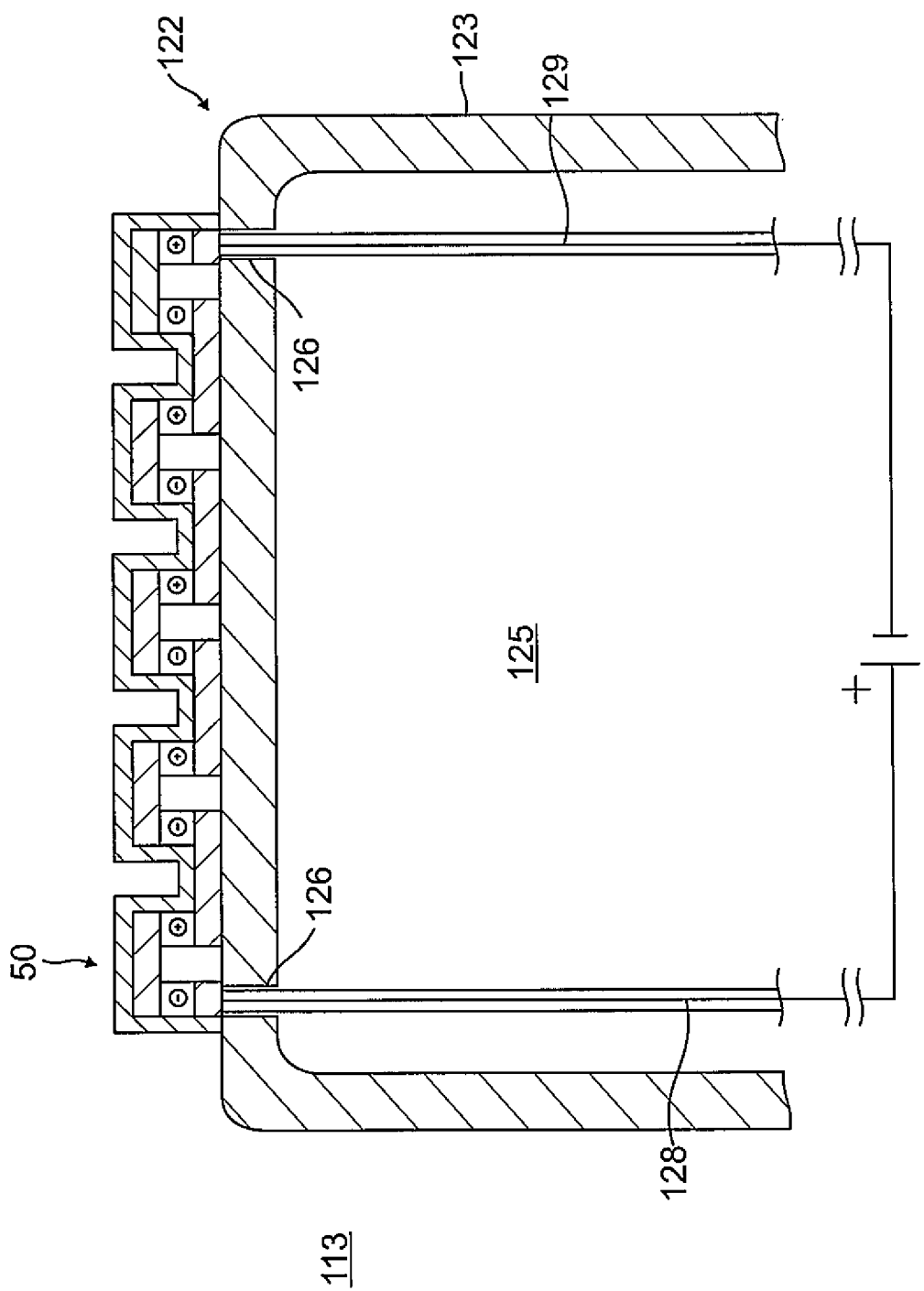
FIG. 12 is a side cross-sectional view of a distal end of a focal cryoablation catheter, according to an embodiment of the present invention.

For a focal catheter 100, the distal tip section 113 whose outer surface supports the MPC modules may be configured as a shell 122 with a sidewall 123 and an interior cavity 125, as shown in FIG. 12, wherein the cavity 125, as an internal heat sink, is adapted to contain circulating cooling fluid passing through feeder and return fluid tubings (not shown), as described above. Hot and neutral lead wires 128 and 129 may extend through the interior cavity 125 and apertures 126 formed in the sidewall 123 for connection to a first MPC unit 50a and a last MPC unit 50n, respectively, of an MPC module 15i. The apertures 126 are sealed and fluid-tight. A thermally and electrically insulating sheath 130 surrounds each wire 128 and 129.

It is understood that for any embodiments of the catheter of the present invention, the "hot" side 41 counterpart to the "cold" side 42 may be the surface on which the MPC units and modules are supported. For example, the balloon membrane 40 of the balloon member 24 or the side wall 123 of the distal tip shell 122 (either as the substrate for the MPC units) may be the "hot" side 41, if they are constructed of a suitable material that is thermally conductive but electrically insulative.

It is also understood that the first and second members 51 and 52 are constructed of material(s) that are both electrically- and thermally-conductive, whereas the "hot" and "cold" layers 41 and 42 are constructed of material(s) that are thermally-conductive but electrically-insulative, so that there is no intended current path through the MPC units from the fluid contained in the interior cavity 125 or from blood or other conductive tissue or bodily fluids near the MPC units. In that regard, the layers 42 may be coextensive in forming a generally contiguous layer that extends over and across the MPC units and modules, sealing them on the substrate and leaving no surface thereof (or at least no surface of conductive components thereof) exposed to unintended current paths. In some embodiments, the membrane 40 is constructed of a thermoplastic material with a low durometer ranging between about 50 A and 55 D, and preferably between about 80 A and 50 D. A suitable material includes Pebax or Pellethane, a medical-grade thermoplastic polyurethane elastomer, with superior resilience, low temperature properties/low thermal conductivity, low electrical conductivity (i.e., insulative dielectric properties), and exceptionally smooth surfaces. Another suitable material is flexible polyimide films.

Suitable materials for lead wires 28, 29, 128 and 129 include electrically conductive materials with low resistivity to prevent Joule heating and undesired loss in cooling efficiency, including, for example, copper.

The N-type and P-type semiconductors may include any thermoelectric material with large Peltier coefficients, including appropriately doped bismuth telluride, silicon-germanium and bismuth-antimony.

The components of the MPC units may be assembled on and/or affixed to the support surface by any suitable methods, including, for example, electrochemical deposition, MEMS (micro-electro-mechanical systems) techniques including photolithography, masking, etching and the like.

Figure 14A:
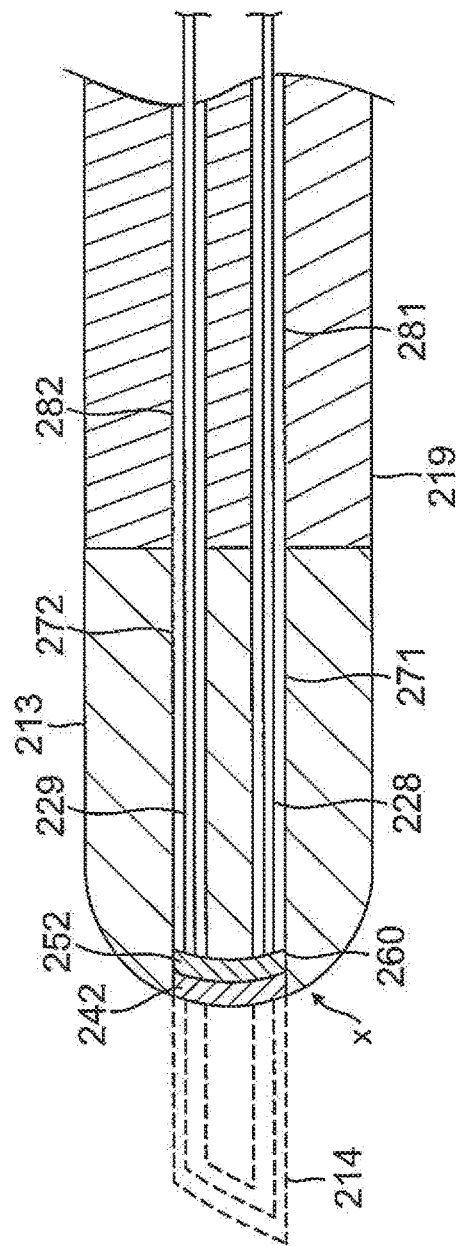
FIG. 14A is a side cross-sectional view of the distal end of FIG. 13.
Figure 14B:
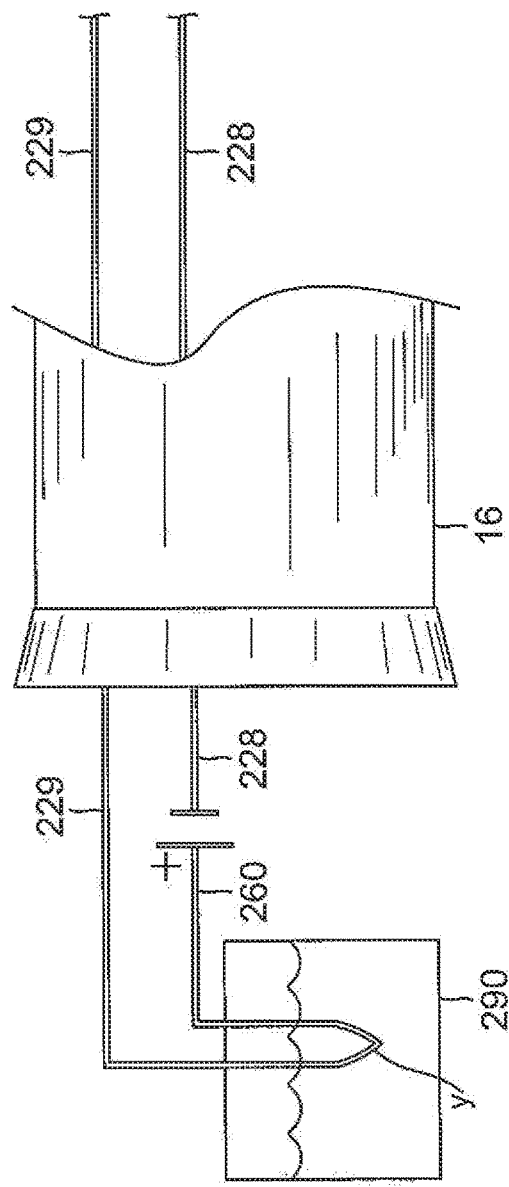
FIG. 14B is a schematic representation of the circuit of the MPC unit of FIG. 13, according to an embodiment of the present invention

FIG. 13, FIG. 14A and FIG. 14B illustrate another embodiment of a focal catheter 200 of the present invention. The catheter 200 has a dome distal tip section 213 having an MPC unit 250, wherein the unit has an N-type wire 228, a P-type wire 229, an electrically conductive inner concave layer 252 (defining a distal or first junction X with distal ends of the wires 228 and 229), and an electrically-insulative and thermally-conductive outer convex layer 242 sealing the layer 252. It is understood that the layer 252 is optional and ed by directly cooling the Y junction The dome distal tip section 213 is made of an electrically-insulative material, and the material may also be thermally-insulative. The layers 252 and 242 are embedded in a recess 260, which may be located, for example, at a distal end of the section 213. In the illustrated embodiment, distal ends the wires 228 and 229 are electrically connected to the layer 252 and extend through respective passages 271 and 272, and through respective lumens 281 and 282 in a tubing 219 proximal of shell 213. The wires 228 and 229 extend through a central lumen of a catheter shaft (not shown) and emerge proximally of the control handle 16 where the proximal or second junction Y of the two wires is thermally coupled to an external heat sink 290, for example, immersed in a bath. Electrified by a voltage/current source 260, with current flowing toward the layer 252 via the N-type wire 228, junction X is configured as the "cold/colder" junction with junction Y configured as the "hot/hotter" junction. With adjustment of the voltage/current, the temperature difference between the junctions X and Y can range between at least about 50 degrees Celsius, preferably at least 60 degrees Celsius, and more preferably about 70 degrees Celsius. Accordingly, where the temperature of the "hot/hotter" junction Y is regulated at about −196 Celsius by the bath 290 containing, for example, liquid nitrogen or liquid carbon dioxide, the temperature of the "cold/colder" junction X can reach about −266 Celsius. Where the bath 290 contains dry ice (with a temperature of about −78.5 Celsius), the temperature of junction X can reach about −148.5 Celsius.

It is understood that in other embodiments the layers 252 and 242 may be configured as an elongated body extending along the longitudinal axis of the distal tip section 213 to resemble and function as a needle 214 (shown in broken lines in FIG. 14A) extending distally from the distal end of the section 213.

Figure 14C:
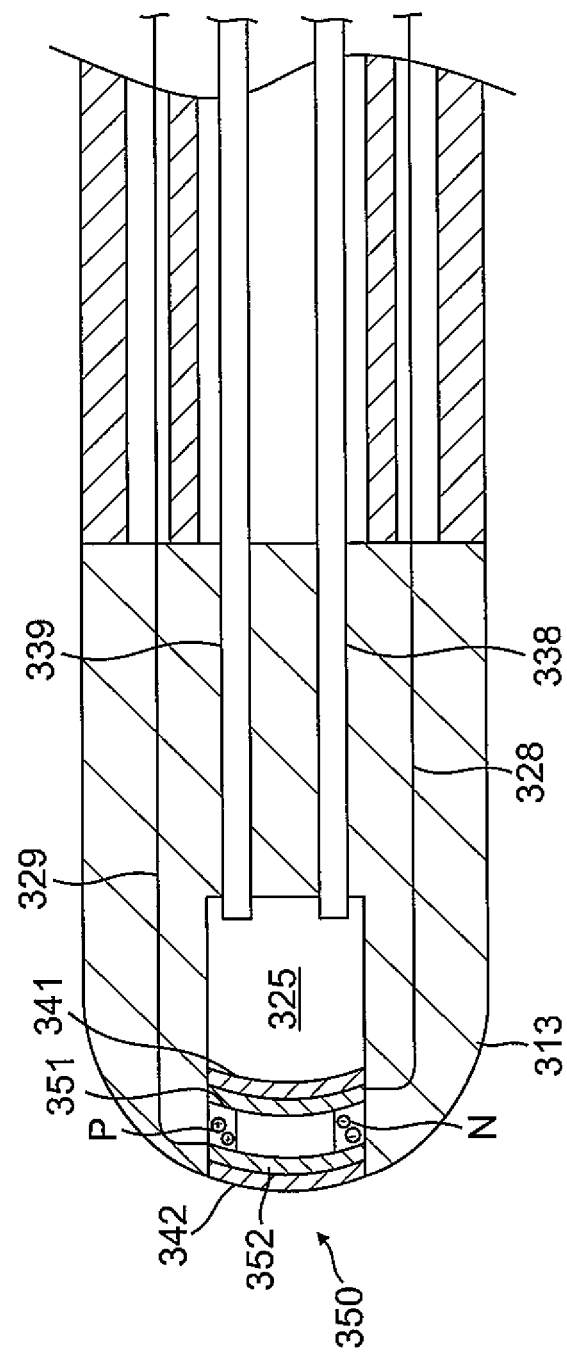
FIG. 14C is a side cross-sectional view of a distal end of a focal cryoablation catheter, according to another embodiment.

As shown in FIG. 14C, another embodiment of a focal catheter 300 is shown with a distal section 313 having an MPC unit 350 and an internal heat sink. The internal heat sink includes an interior cavity 325 that is circulated with a fluid of a predetermined temperature that enters and exits the interior cavity 325 via feeder and return fluid tubings 338 and 339.

The MPC unit 350 has an N-type semiconductor N and a P-type semiconductor P that are configured thermally in parallel to each other by thermally-conducting, electrically insulative proximal and distal layers or surfaces 341 and 342, and electrically in series at cold and hot junctions X and Y defined by, respectively, first and second electrically-conducting members 351 and 352 at their opposing ends. The tissue contact surface of the catheter includes the distal layer or surface 342.

Hot lead wire 328 is electrically connected to the N-type semiconductor N and the neutral lead wire 329 is electrically connected to the P-type semiconductor P, such that the first member 351 is the hot side or junction and the second member 352 is the cold side or junction of the MPC unit 350. The thermally-conducting, electrically insulative layers 341 and 342 prevent any unintended current path through the MPC unit from fluid contained in the interior cavity 325 or from blood or other conductive tissue or bodily fluids near the MPC units.

The first member 351 or hot side is in closer proximity to the interior cavity 325 as a heat sink such that its temperature is regulated by the fluid contained in the interior cavity 325 via thermal conduction across the layer 341. Thus, the second member 352 presenting the cold side is in closer proximity to the distal layer 342 which is configured for tissue contact.

It is understood that the catheter 313 may include any number of MPC units 350 sharing the interior cavity 325 and fluid as their common heat sink, wherein the respective second members 352 of the units 350 are presented as the cold side for tissue contact.

Figure 15A:
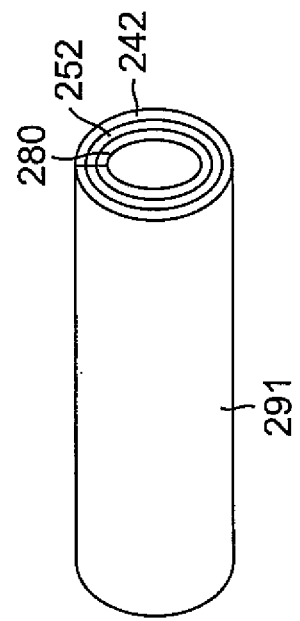
FIG. 15A is a perspective view of a "cold" junction having a layered construction.
Figure 15B:
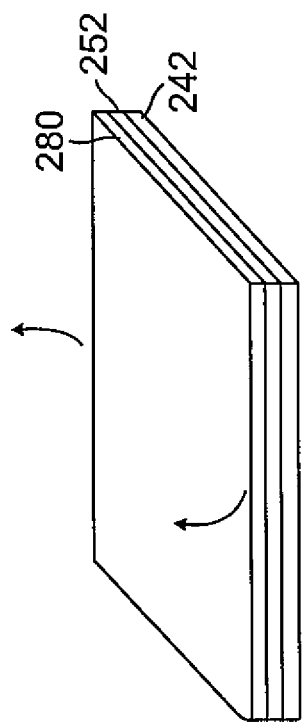
FIG. 15B is a perspective view of the layered construction of FIG. 15A being rolled into a cylindrical body.
Figure 16:
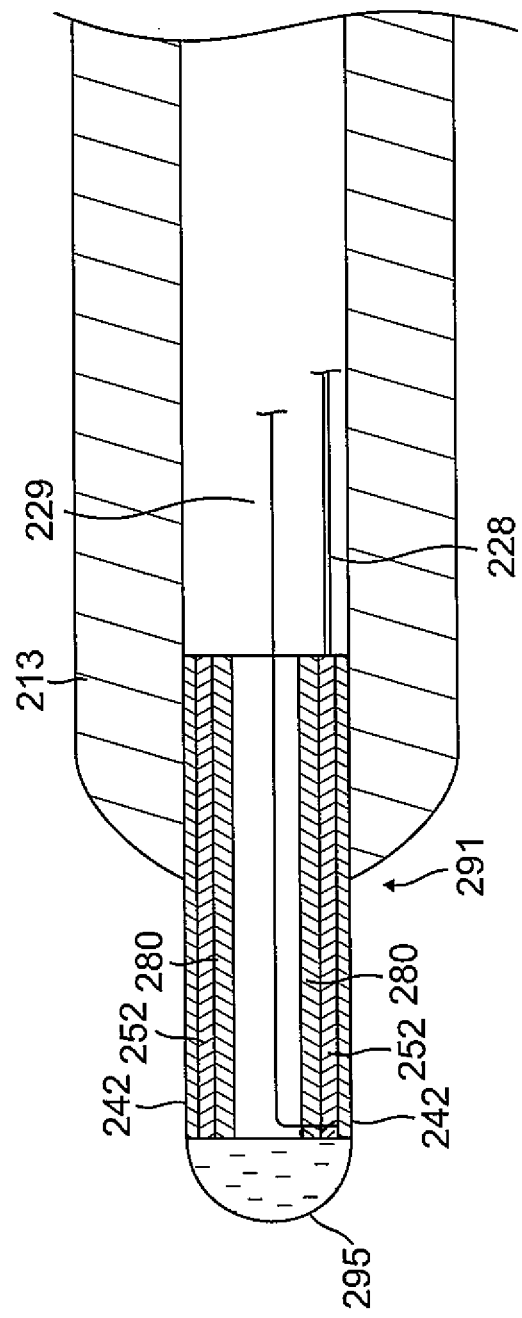
FIG. 16 is a side cross-sectional view of a distal tip of a catheter including the "cold" junction cylindrical body of FIG. 16B.

In yet other embodiments, the layers 252 and 242 may be deposited electrochemically on a flexible polyimide film 280, as shown in FIG. 15A, rolled into a cylindrical body 291, with the layer 252 facing outwardly and the film 280 facing inwardly, as shown in FIG. 15B, and assembled as component of a tip section 213 extending longitudinally and distally of the tip section 213, as shown in FIG. 16. A distal end of the cylindrical body 291 may be capped and sealed with a sealant 295, for example, polyurethane or epoxy.

As part of an MPC circuit, the wires 228 and 229 are constructed of electrical conductors. In some embodiments, one or both of these wires may be constructed of drawn and appropriately-doped bismuth telluride, silicon-germanium and bismuth-antimony, for example, N-doped bismuth telluride for an N-type wire 228 and P-doped bismuth telluride for P-type wire 229.

It is understood that the present invention includes embodiments wherein the voltage/current source and the MPC components and/or circuit are configured such that the current direction is in the opposite direction, where the hot side faces outwardly or is the outer contact surface and the cold side faces inwardly or is the inner surface of the distal portion of the catheter, as desired or appropriate.

The preceding description has been presented with reference to presently disclosed embodiments of the invention. Workers skilled in the art and technology to which this invention pertains will appreciate that alterations and changes in the described structure may be practiced without meaningfully departing from the principal, spirit and scope of this invention. As understood by one of ordinary skill in the art, the drawings are not necessarily to scale and any feature or combinations of features described in any one embodiment may be incorporated into any other embodiments or combined with any other feature(s) of other embodiments, as desired or needed. Accordingly, the foregoing description should not be read as pertaining only to the precise structures described and illustrated in the accompanying drawings, but rather should be read consistent with and as support to the following claims which are to have their fullest and fair scope.

What is claimed is:

1. An electrophysiology catheter for use in a patient's vasculature, comprising:
    an elongated catheter body; and
    a distal section configured for tissue contact, the distal section having:
        a plurality of micro-Peltier cooling modules arranged on a thermally-conductive and electrically-nonconductive substrate, each of the plurality of micro-Peltier cooling modules comprising a plurality of micro-Peltier cooling units cascaded together, each of the plurality of micro-Peltier cooling units having a hot junction and a cold junction;
        a common exposed thermally-conductive and electrically-nonconductive layer covering the plurality of micro-Peltier cooling modules and configured for tissue contact, the common exposed thermally-conductive and electrically-nonconductive layer sealing the cold junction of each of the plurality of micro-Peltier cooling units from exposure to blood in the vasculature, the thermally-conductive and electrically-nonconductive substrate supporting the plurality of micro-Peltier cooling modules such that the hot junction of each of the plurality of micro-Peltier cooling units is in closer proximity to the thermally-conductive and electrically-nonconductive substrate, and the cold junction of each of the plurality of micro-Peltier cooling units is in closer proximity to the exposed thermally-conductive and electrically-nonconductive layer; and
        an interior cavity configured to receive a fluid having a predetermined temperature, the interior cavity configured to position the fluid for thermal conduction between the fluid and the hot junction of each of the plurality of micro-Peltier cooling units across the thermally-conductive and electrically-nonconductive substrate, and the exposed thermally-conductive and electrically-nonconductive layer being on an outer surface of the interior cavity;
    the catheter configured for current flow through the cold and hot junctions of each of the plurality of micro-Peltier cooling units, each of the plurality of micro-Peltier cooling units configured to provide a temperature difference between the hot junction and the cold junction of each of the plurality of micro-Peltier cooling units of about 50 degrees or greater upon application of a current.

2. The catheter of claim 1, wherein the current flows from a first N-type semiconductor to a last P-type semiconductor.

3. The catheter of claim 1, wherein the distal section includes an inflatable balloon member having a membrane defining the interior cavity, at least a portion of the membrane forming the thermally-conductive and electrically-nonconductive substrate, and the exposed thermally-conductive and electrically-nonconductive layer being positioned on an outer surface of the membrane.

4. The catheter of claim 1, wherein the distal section includes a distal tip shell having a shell wall defining the interior cavity, at least a portion of the shell wall forming the thermally-conductive and electrically-nonconductive substrate, and the exposed thermally-conductive and electrically-nonconductive layer being positioned on an outer surface of the shell wall.

5. The catheter of claim 1, wherein the cold junction of each of the plurality of micro-Peltier cooling units includes an electrically-conductive material, preceded by an N-type semiconductor material, and followed by a P-type semiconductor material, connected in series.

6. The catheter of claim 1, wherein the hot junction of each of the plurality of micro-Peltier cooling units includes an electrically-conductive material, preceded by a P-type semiconductor material, and followed by an N-type semiconductor material, connected in series.

7. The catheter of claim 5, wherein the P-type semiconductor material comprises at least one of bismuth telluride, silicon-germanium and bismuth-antimony; and the N-type semiconductor material comprises at least one of bismuth telluride, silicon-germanium and bismuth-antimony.

8. The catheter of claim 6, wherein the P-type semiconductor material comprises at least one of bismuth telluride, silicon-germanium and bismuth-antimony; and the N-type semiconductor material comprises at least one of bismuth telluride, silicon-germanium and bismuth-antimony.

9. The catheter of claim 1, wherein the temperature of the fluid ranges between about 10 degrees Celsius and −10 degrees Celsius.

10. The catheter of claim 1, wherein the catheter further comprises a control handle and a voltage/current source housed in the control handle.

11. An electrophysiology catheter for insertion into a patient's vasculature, comprising:
    an elongated catheter body;
    a distal section distal of the elongated catheter body, the distal section having proximal and distal ends and having an outer surface layer configured for contact with tissue, the outer surface layer being thermally conductive and electrically nonconductive;

a control handle proximal of the elongated catheter body;
a micro-Peltier cooling unit, the micro-Peltier cooling unit having:
- a first wire of a first material having a distal end in the distal section, and a proximal end proximal of the distal section;
- a second wire of a second material having a distal end in the distal section, and a proximal end proximal of the distal section;
- a cold junction comprising:
  - an electrically conductive inner layer embedded in a recessed portion of a distal face of the distal end of the distal section and connecting the distal ends of the first and second wires, and
  - an electrically-nonconductive and thermally conductive outer layer embedded in the recessed portion of the distal face of the distal end of the distal section and sealing the electrically conductive inner layer in the recessed portion of the distal face of the distal end of the distal section such that the cold junction is positioned in the distal section and thermally coupled to the outer surface layer of the distal section via the electrically-nonconductive and thermally conductive outer layer;
- a hot junction comprising an electrically conductive connection of the proximal ends of the first and second wires, the hot junction positioned proximally of the cold junction; and
- a heat sink thermally coupled to the hot junction, the heat sink having a predetermined temperature; and
the catheter configured for current flow through the micro-Peltier cooling unit.

12. The catheter of claim 11, wherein the hot junction is proximal of the control handle.

13. The catheter of claim 11, wherein the heat sink includes a fluid reservoir.

14. The catheter of claim 11, wherein the predetermined temperature of the heat sink ranges between about 10 degrees Celsius and −10 degrees Celsius.

15. The catheter of claim 11, wherein the first material includes an N-type semiconductor material comprising at least one of bismuth telluride, silicon-germanium and bismuth-antimony.

16. The catheter of claim 11, wherein the first material includes a P-type semiconductor material comprising at least one of bismuth telluride, silicon-germanium and bismuth-antimony.

17. An electrophysiology catheter for insertion into a patient's vasculature, comprising:
an elongated catheter body;
a distal section distal of the elongated catheter body, the distal section having proximal and distal ends and having a distal probe portion with an outer surface layer configured for tissue contact, the outer surface layer being thermally-conductive and electrically-nonconductive; and
a control handle proximal of the elongated catheter body, the distal probe portion further comprising a micro-Peltier cooling unit, the micro-Peltier cooling unit having:
- a first wire of a first material having a distal end in the distal section, and a proximal end proximal of the distal section;
- a second wire of a second material having a distal end in the distal section, and a proximal end proximal of the distal section;
- a cold junction comprising an inner electrically-conductive material and an outer electrically-nonconductive and thermally conductive material in a tubular configuration having a proximal end in a recess in a distal face of the distal end of the distal section:
  - the inner electrically-conductive material coupling the distal ends of the first and second wires, and
  - the outer electrically-nonconductive and thermally conductive material sealing the inner electrically-conductive material, and the cold junction thermally coupled to the outer surface layer;
- a hot junction comprising an electrically conductive connection of the proximal ends of the first and second wires, the hot junction positioned proximally of the cold junction; and
- a heat sink thermally coupled to the hot junction, the heat sink having a predetermined temperature.

18. The catheter of claim 17, wherein the first material includes an N-type semiconductor material comprising at least one of bismuth telluride, silicon-germanium and bismuth-antimony.

19. The catheter of claim 17, wherein the first material includes a P-type semiconductor material comprising at least one of bismuth telluride, silicon-germanium and bismuth-antimony.

20. The catheter of claim 17, wherein the tubular configuration comprises a distal needle having a distal end extending beyond the distal end of the distal section.

* * * * *